United States Patent
Kellar et al.

(10) Patent No.: US 11,278,522 B2
(45) Date of Patent: Mar. 22, 2022

(54) USE OF METHADONE METABOLITES FOR TREATMENT OF ANXIETY AND DEPRESSION

(71) Applicant: Georgetown University, Washington, DC (US)

(72) Inventors: Kenneth J. Kellar, Bethesda, MD (US); Yingxian Xiao, Potomac, MD (US); Patrick A. Forcelli, Washington, DC (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 16/927,544

(22) Filed: Jul. 13, 2020

(65) Prior Publication Data

US 2021/0161861 A1    Jun. 3, 2021

Related U.S. Application Data

(62) Division of application No. 15/577,550, filed as application No. PCT/US2016/034979 on May 31, 2016, now Pat. No. 10,709,685.

(60) Provisional application No. 62/167,505, filed on May 28, 2015.

(51) Int. Cl.
   *A61K 31/40*    (2006.01)
   *A61P 25/24*    (2006.01)
   *A61P 25/22*    (2006.01)
   *A61K 9/00*    (2006.01)

(52) U.S. Cl.
   CPC ............ *A61K 31/40* (2013.01); *A61K 9/0053* (2013.01); *A61P 25/22* (2018.01); *A61P 25/24* (2018.01)

(58) Field of Classification Search
   CPC ............................... A61K 31/40; A61P 25/24
   See application file for complete search history.

(56) References Cited

U.S. PATENT DOCUMENTS

| | | |
|---|---|---|
| 10,709,685 B2 | 7/2020 | Kellar et al. |
| 2007/0129434 A1 | 6/2007 | Smith-Carliss et al. |
| 2008/0058345 A1 | 3/2008 | George et al. |
| 2018/0169065 A1 | 6/2018 | Kellar et al. |

OTHER PUBLICATIONS

International Preliminary Report on Patentability in Application No. PCT/US2016/034979 dated Nov. 28, 2017.

*Primary Examiner* — Theodore R. Howell
(74) *Attorney, Agent, or Firm* — Foley Hoag LLP; Dana M. Gordon

(57) ABSTRACT

Previous studies (Xiao et al., 2001) have identified two metabolites of methadone, EMDP (2-ethyl-5-methyl-3,3-diphenyl-1-pyrroline) and EDDP (2-ethylidene-1,5-dimethyl-3,3-diphenylpyrrolidine), which are considered to be inactive at opiate receptors, as relatively potent noncompetitive channel blockers of $\alpha 3\beta 4$ nAChRs. We have now evaluated these compounds in rats and mice in preclinical behavioral models predictive of potential anxiolytic and antidepressant efficacy. We found that EMDP, but not EDDP, displayed robust effects predictive of anxiolytic and antidepressant efficacy without significant effects on locomotor activity. Moreover, EMDP at behaviorally active doses, unlike mecamylamine, did not produce eyelid ptosis, suggesting it may produce fewer autonomic side effects than mecamylamine. Thus, the methadone metabolite EMDP may represent a novel therapeutic avenue for the treatment of some affective disorders.

4 Claims, 9 Drawing Sheets

USE OF METHADONE METABOLITES FOR TREATMENT OF ANXIETY AND DEPRESSION

CROSS REFERENCE TO RELATED APPLICATIONS

This application is a divisional of U.S. patent application Ser. No. 15/577,550, filed Nov. 28, 2017, which is the U.S. national phase of International Patent Application No. PCT/US16/034979, filed May 31, 2016, which claims benefit of priority to U.S. Provisional Application No. 62/167,505, filed May 28, 2015.

GOVERNMENT SUPPORT

This invention was made with government support under grants CA143187, GM008076, DA032681, HD046388, and DA027990 awarded by the National Institutes of Health. The government has certain rights in the invention.

BACKGROUND OF THE INVENTION

Anxiety and depression are the two most common mental health disorders, impacting ~25% of the US population per year (Kessler et al., 2005). While the treatment of affective disorders has improved substantially since the introduction of drugs such as selective monoaminergic reuptake inhibitors, one-third of individuals with these disorders remain treatment resistant (Trivedi et al., 2006). Furthermore, adverse side effects of these drugs limit their use in some patients. These issues with conventional pharmacotherapy for affective disorders underscore the need for drugs aimed at new targets for the treatment anxiety and depression. Neuronal nicotinic acetylcholine receptors (nAChRs) may be one such target.

The enhancement of GABAergic and monoaminergic neurotransmission has been the mainstay of pharmacotherapy and the focus of drug discovery for anxiety and depressive disorders for several decades. However, the significant limitations of drugs used for these disorders underscore the need for novel therapeutic targets. Neuronal nicotinic acetylcholine receptors (nAChRs) may represent one such target. For example, nicotine elicits anxiolytic effects in rodent models, and mecamylamine, a non-competitive antagonist of nAChRs, displays positive effects in preclinical tests for anxiolytic and antidepressant activity in rodents.

SUMMARY OF THE INVENTION

Methadone has a long record of use in humans (>50 years) as an analgesic and as an orally effective replacement to treat heroin addiction. It has an apparently excellent safety record, so presumably its metabolites 2-ethylidene-1,5-dimethyl-3,3-diphenylpyrrolidine (EDDP) and 2-ethyl-5-methyl-3,3-diphenyl-1-pyrroline (EMDP) are also relatively safe. Our data, in this broader clinical framework, suggest that EMDP through blockade of nAChRs and/or even previously unrecognized actions at opiate receptors may have therapeutic potential as an anxiolytic and/or antidepressant agent meriting further clinical evaluation.

In summary, the findings here demonstrate that the methadone metabolites EMDP and EDDP are pharmacologically active at nAChRs in vitro and behaviorally active in vivo in preclinical tests for anxiolytic and antidepressant activity. These studies provide preclinical support for and suggest the use of EMDP, in particular, as a potential treatment for affective disorders. Importantly, since humans have been exposed both acutely and chronically to EMDP as a metabolite of methadone for more than 50 years, a trial of its clinical utility as an anxiolytic and/or antidepressant is warranted and should be relatively straightforward.

An aspect of the invention is a method of treating anxiety, comprising administering to a subject in need thereof a therapeutically effective amount of a compound selected from the group consisting of 2-ethyl-5-methy-3,3-diphenyl-1-pyrroline (EMDP), 2-ethylidene-1,5-dimethyl-3,3-diphenylpyrrolidine (EDDP), and pharmaceutically acceptable salts thereof.

An aspect of the invention is a method of treating depression, comprising administering to a subject in need thereof a therapeutically effective amount of a compound selected from the group consisting of 2-ethyl-5-methyl-3,3-diphenyl-1-pyrroline (EMDP), 2-ethylidene-1,5-dimethyl-3,3-diphenylpyrrolidine (EDDP), and pharmaceutically acceptable salts thereof.

In certain embodiments, the compound is EMDP or a pharmaceutically acceptable salt thereof.

In certain embodiments, the compound is EDDP or a pharmaceutically acceptable salt thereof.

In certain embodiments, the subject is a human.

In certain embodiments, the subject is not in need of treatment for opioid (narcotic) addiction.

In certain embodiments, the compound is administered orally.

DETAILED DESCRIPTION OF THE INVENTION

Figure 1:
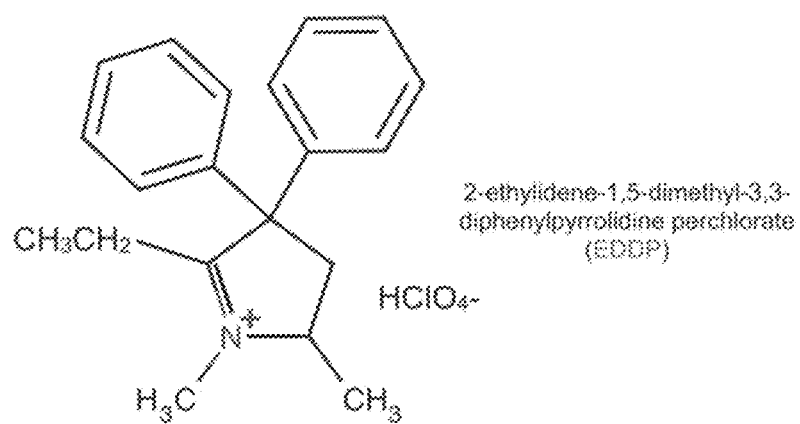
FIG. 1. Chemical structures of EDDP and EMDP. Note that the structural difference between the two compounds is a single methyl group and the charge on the associated quaternary nitrogen.
Figure 1:
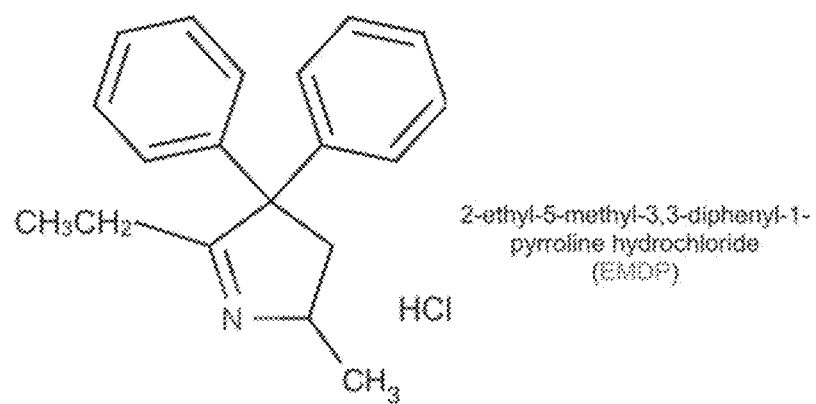
Figure 2:
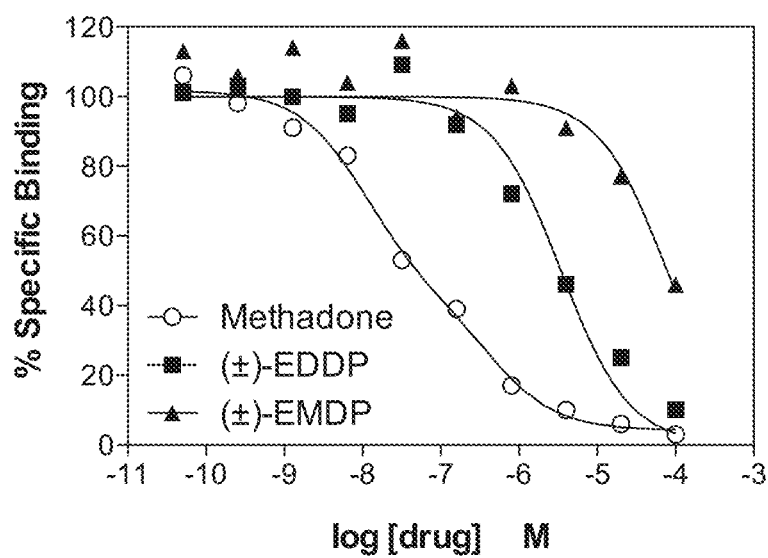
FIG. 2. Methadone, EDDP and EMDP competition for opiate receptor binding sites labeled by [$^3$H]-naloxone in rat forebrain membranes. Opiate receptors in rat forebrain (colliculi forward) were labeled by 2 nM [$^3$H]-naloxone ($K_d$ is ~0.7 nM) in the absence or presence of (−)-methadone, (±)-EDDP or (±)-EMDP at the concentrations shown. Methadone competition curves fit a model for two sites, with the largest fraction having an affinity of 11 nM. EDDP and EMDP completion curves fit a model for a single binding site. EDDP competed for nearly all of the binding sites but with an apparent affinity ~83-fold lower than that of methadone. EMDP competed for only 60% of the sites even at a concentration of 100 μM, and its apparent affinity was ~1900-fold lower than that of methadone. The $K_i$ values for EDDP and EMDP were 918 nM and 21 μM, respectively. The results shown are representative of two independent assays.

Anxiety and depression are both highly co-morbid with nicotine dependence (Glassman et al., 1990; Paperwalla et al., 2004; Bertrand, 2005; Zvolensky et al., 2008; Mineur and Picciotto, 2010), suggesting that nicotine use may in part be an attempt at self-medication in these conditions. Indeed, nicotine produces effects consistent with anxiolytic (File et al., 1998; Turner et al., 2010, 2011; McGranahan et al., 2011; Anderson and Brunzell, 2012; Hussmann et al., 2014) and antidepressant activity (Tizabi et al., 1999; Ferguson et al., 2000; Vázquez-Palacios et al., 2005) in preclinical rodent models. Nicotine also increases the rate of adult neurogenesis (Mudò et al., 2007; Belluardo et al., 2008), a proposed biomarker of antidepressant efficacy common to clinically utilized antidepressant drugs (Eisch and Petrik, 2012).

nAChRs are pentameric ligand-gated ion channels comprised from nine $\alpha$ and three $\beta$ subunits that are widely expressed throughout the nervous system. While peripheral nAChRs have a direct, fast excitatory signaling role at ganglia, in the brain, these receptors are frequently associated with regulation of the release of neurotransmitters, including dopamine norepinephrine, acetylcholine, GABA, glutamate and possibly serotonin (McKay et al., 2007). Thus, drugs targeting nAChRs have the potential to modulate multiple brain pathways, including those involved in complex behaviors and affect. Interestingly, mecamylamine, a noncompetitive blocker of nAChR channels, also displays positive effects in preclinical tests for anxiolytic and anti-depressant activity in rodents (Rabenstein et al., 2006; Lippiello et al., 2008; Nickell et al., 2013), and it was initially reported to have antidepressant and anxiolytic effects in preliminary human trials (Shytle et al., 2002; Bacher et al., 2009; but see Ledford, 2011).

Two compounds of interest are the methadone primary N-demethylated metabolite, EDDP, and its trace secondary N-demethylated derivative, EMDP. Both compounds are believed to be inactive at opiate receptors (Pohland et al., 1971), but both potently block rat $\alpha 3\beta 4$ nAChR channels (Xiao et al., 2001). The effects of EDDP and EMDP on affective behaviors in vivo are unknown. Therefore, to evaluate whether EDDP and/or EMDP exert anxiolytic-like and/or antidepressant-like activities in vivo, we tested their efficacy in preclinical paradigms sensitive to anxiolytic or antidepressant drugs. We found that EMDP and, to a lesser degree, EDDP displayed anxiolytic-like activity. Furthermore, EMDP also displayed antidepressant-like activity. Interestingly, eyelid ptosis, an indicator of ganglionic side effects, was present following behaviorally active doses of mecamylamine, but not EMDP, suggesting that EMDP may produce fewer autonomic side effects compared to mecamylamine.

As disclosed herein, it has now been surprisingly discovered by the inventors that EMDP is superior in its anxiolytic and anti-depressive efficacy compared to EDDP, despite the latter compound's superior inhibition of nAChR.

An aspect of the invention is a method of treating anxiety, comprising administering to a subject in need thereof a therapeutically effective amount of a compound selected from the group consisting of 2-ethyl-5-methyl-3,3-diphenyl-1-pyrroline (EMDP), 2-ethylidene-1,5-dimethyl-3,3-diphenylpyrrolidine (EDDP), and pharmaceutically acceptable salts thereof.

In certain embodiments, the compound is EMDP or a pharmaceutically acceptable salt thereof.

In certain embodiments, the compound is EDDP or a pharmaceutically acceptable salt thereof.

In certain embodiments, the subject is a human.

In certain embodiments, the subject is not in need of treatment for opioid (narcotic) addiction. For example, in certain embodiments, the subject is not in need of treatment for heroin addiction.

In certain embodiments, the compound is administered orally.

An aspect of the invention is a method of treating depression, comprising administering to a subject in need thereof a therapeutically effective amount of a compound selected from the group consisting of 2-ethyl-5-methyl-3,3-diphenyl-1-pyrroline (EMDP), 2-ethylidene-1,5-dimethyl-3,3-diphenylpyrrolidine (EDDP), and pharmaceutically acceptable salts thereof.

In certain embodiments, the compound is EMDP or a pharmaceutically acceptable salt thereof.

In certain embodiments, the compound is EDDP or a pharmaceutically acceptable salt thereof.

In certain embodiments, the subject is a human.

In certain embodiments, the subject is not in need of treatment for opioid (narcotic) addiction. For example, in certain embodiments, the subject is not in need of treatment for heroin addiction.

In certain embodiments, the compound is administered orally.

Dosing and Formulation

Methadone, which is a precursor molecule of EMDP and EDDP, typically is administered orally to human subjects in a dose of 5 to 15 mg per day for analgesic use. Specialized dosage forms used in opioid addiction include tablets containing 2.5, 5, 10, or 40 mg of methadone. It is expected that effective doses or dosing of EMDP and EDDP in humans will be similar to doses or dosing of methadone, e.g., 2.5 to 40 mg per day when administered orally.

The active compound or other therapeutics may be administered alone (e.g., in saline or buffer) or using any delivery vehicles known in the art.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular active compound being administered, the size of the subject, or the severity of the disease or condition. One of ordinary skill in the art can empirically determine the effective amount of a particular active compound and/or other therapeutic agent without necessitating undue experimentation.

For adult human subjects, doses of the active compounds described herein typically range from about 1 mg/dose to about 100 mg/dose, more typically from about 5 mg/dose to about 40 mg/dose, and most typically from about 10 mg/dose to about 20 mg/dose. Doses will depend on factors including the route of administration, e.g., oral administration may require a substantially larger dose than subcutaneous or other parenteral administration.

The active compounds of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The active compound can be given in conjunction with other agents known in the art to be useful in the treatment of anxiety or depression.

For use in therapy, an effective amount of the active compound can be administered to a subject by any mode that delivers the active compound to the desired site, e.g., mucosal, systemic. "Administering" the pharmaceutical composition of the present invention may be accomplished by any means known to the skilled artisan. Preferred routes of administration include but are not limited to oral, subcutaneous, intramuscular, intranasal, intratracheal, inhalational, and rectal.

For oral administration, the compounds (i.e., active compound or compounds) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas. e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer *Science* 249:1527 (1990), which is incorporated herein by reference.

The active compound(s) may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulfuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2 percent w/v); citric acid and a salt (1-3 percent w/v); boric acid and a salt (0.5-2.5 percent w/v); and phosphoric acid and a salt (0.8-2 percent w/v). Suitable preservatives include benzalkonium chloride (0.003-0.03 percent w/v); chlorobutanol (0.3-0.9 percent w/v); parabens (0.01-0.25 percent w/v) and thimerosal (0.004-0.02 percent w/v).

The pharmaceutical compositions of the invention contain an effective amount of an active compound and optionally other therapeutic agents optionally included in a pharmaceutically-acceptable carrier. The term "pharmaceutically-acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

A variety of administration routes are available. The particular mode selected will depend, of course, upon the particular active compound selected, the particular condition being treated, and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed above.

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories. For treatment of a patient, depending on activity of the compound, manner of administration, purpose of the administration (i.e., prophylactic or therapeutic), nature and severity of the disorder, age and body weight of the patient, different doses may be necessary. The administration of a given dose can be carried out both by single administration in the form of an individual dose unit or else several smaller dose units.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer-based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fait) acids or neutral fats such as mono-, di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Having now described the present invention in detail, the same will be more clearly understood by reference to the following examples, which are included herewith for purposes of illustration only and are not intended to be limiting of the invention.

EXAMPLES

Materials and Methods

Stable cell lines and $^{86}Rb^+$ efflux Assay. The cell lines expressing human α4β2 (YXα4β2H1) and α3β4 (YXα3β4H1) nAChRs were established recently (Xiao el al., 2012). These cell lines were maintained in minimum essential medium (MEM) supplemented with 10% fetal bovine serum, 100 units/mL penicillin G, 100 mg/mL streptomycin and selective antibiotics at 37° C. with 5% $CO_2$ in a humidified incubator. Tissue culture medium and antibiotics were obtained from Invitrogen Corporation (Carlsbad, Calif.), unless otherwise stated. Fetal bovine serum was obtained from Gemini Bio-Products (Woodland, Calif.).

Functional properties of compounds at nAChRs expressed in the transfected cells were measured using $^{86}Rb^+$ efflux assays as described previously (Xiao et al., 1998, 2001). In brief, cells were plated into 24-well plates coated with poly-D-lysine. The plated cells were grown at 37° C. for 18 to 24 hour to reach 85-95% confluence. The cells were then incubated in growth medium (0.5 mL/well) containing $^{86}Rb^+$ (2 µCi/mL) for 4 hour at 37° C. The loading mixture was then aspirated, and the cells were washed four times with 1 mL buffer (15 mM HEPES, 140 mM NaCl, 2 mM KCl, 1 mM MgSO4, 1.8 mM CaCl2), 11 mM Glucose, pH 7.4). One mL of buffer with or without compounds to be tested was then added to each well. After incubation for 2 min, the assay buffer was collected for measurements of $^{86}Rb^+$ released from the cells. Cells were then lysed by adding 1 mL of 100 mM NaOH to each well, and the lysate was collected for determination of the amount of $^{86}Rb^+$ that was in the cells at the end of the efflux assay. Radioactivity of assay samples and lysates was measured by liquid scintillation counting. Total loading (cpm) was calculated as the sum of the assay sample and the lysate of each well, and the amount of $^{86}Rb^+$ efflux was expressed as a percentage of $^{86}Rb^+$ loaded. Stimulated $^{86}Rb^+$ efflux was defined as the difference between efflux in the presence and absence of nicotine. To obtain $IC_{50}$ values, inhibition curves were constructed in which increasing concentrations of a compound were included in the assay to inhibit efflux stimulated by 100 µM nicotine. IC50 values were determined by nonlinear least-squares regression analyses (GraphPad. San Diego, Calif.).

[$^3$H]-Naloxone binding assay. Rat forebrain (from colliculi forward) was weighed, suspended in cold 50 mM Tris-HCl buffer (pH 7.4) containing 100 mM NaCl and homogenized with a polytron homogenizer. The homogenate was centrifuged at 35,000 g for 10 min, the pellet was resuspended in fresh buffer, centrifuged again, and the final pellet resuspended in buffer. Aliquots equivalent to 10 mg of original tissue weight (~500 µg protein) were added to tubes containing 2 nM [$^3$H]-naloxone (53.7 Ci/mmol; Perkin Elmer, Inc. Boston, Mass.) and a range of concentrations of methadone, EMDP or EDDP in a final volume of 1 mL. The tubes were incubated for 1 h at 24° C. and then filtered over GF/C filters pre-wet with polyethyleneimine and mounted on a Brandel cell harvester. The filters were washed 3 times with buffer, placed in vials and then counted in a Beckman scintillation counter. Non-specific binding was measured in the presence of 10 µM unlabeled naloxone or 100 µM methadone (which gave similar values). Specific binding was defined as the difference between total and nonspecific binding. Competition curves for each added drug were analyzed with GraphPad Prism 5 (GraphPad Software, Inc. San Diego, Calif.).

Rats. Adult, male Sprague-Dawley rats (225-300 g at the start of the study; Harlan Labs) were housed in a temperature-controlled vivarium (22° C.) at Georgetown University Medical Center and maintained on a standard 12-hr, light-dark cycle (lights on from 6 a.m.-6 p.m.), with food and water available ad libitum. All experimental manipulations were performed during the light phase. All procedures were completed with approval from the Georgetown University Animal Care and Use Committee and in accordance with AALAC recommendations and the Guide for Care and Use of Laboratory Animals (National Research Council (U.S.) et al., 2011).

Mice. Adult male 129SvEv;C57Bl/6J F1 hybrid mice (7-10 weeks of age; 25-35 g; Taconic) were group-housed and maintained on a 12 h light/dark cycle with food and water available ad libitum. We have previously used this mouse strain when investigating behavioral effects of nicotinic modulators (Turner et al., 2010, 2011, 2013; Hussmann et al., 2014). All experimental testing sessions were conducted between 9:00 A.M. and 3:00 P.M., with animals randomly assigned to treatment conditions and tested in counterbalanced order. All procedures with mice were completed with approval from the University of Pennsylvania Animal Care and Use Committee.

Drugs and Treatments. The following compounds were generously provided by Research Triangle Institute (Research Triangle Park, N.C.) through the National Institute on Drug Abuse: (+)EDDP, (−)EDDP and racemic EDDP [2-ethylidene-1,5,dimethyl-3,3-diphenylpyrrolidine perchlorate], and (+), (−) and racemic EMDP [2-ethyl-5-methyl-3,3-diphenyl-1-pyrroline hydrochloride], The structures of EDDP and EMDP are shown in FIG. 1. Note that EDDP carries a positive charge.

Mecamylamine HCl, sertraline HCl, chlordiazepoxide HCl (CDP) and (−)-nicotine hydrogen tartrate were purchased from Sigma-Aldrich (St. Louis, Mo.).

All drugs doses in animal studies are expressed as milligrams per kilogram of the salt form. Racemic EMDP and EDDP were used for behavioral studies. For rat studies, drugs were dissolved in 1:1 DMSO:Saline and administered subcutaneously (s.c.). For mouse studies, drugs were dissolved in 0.9% saline and injected intraperitoneally (i.p.).

Behavioral Assays. Animals were transported from the animal facility to testing rooms, where they were allowed to acclimate for a minimum of 30 minutes prior to the onset of behavioral testing. All behavioral testing was conducted and scored while blind to treatment conditions.

Locomotor Activity (Rats) Locomotor activity was measured 30 minutes after sc injection of test compound. Animals were placed in a Plexiglass enclosure (16"×16"×16", TruScan Arena, Coulbourn Instruments, Whitehall, Pa.) with 770 lux illumination over the center of the arena. Animals were allowed to explore for 20 min, during which total distance traveled was recorded using ANYmaze software (Stoelting Co., Wood Dale, Ill.), as previously described (Forcelli et al., 2012).

Locomotor Activity (Mice) Locomotor activity in response to i.p. drug administration was analyzed in a "home cage" activity monitoring system (Med Associates, St. Albans, Vt.), as previously described (Walters and Blendy, 2001; Mackler et al., 2008; Isiegas et al., 2009). Briefly, a novel cage identical to the home cage (28.9 cm×17.8 cm 12 cm) was placed in a photo-beam frame (30 cm×24 cm×8 cm) with sensors arranged in an 8-beam array strip. For dose studies, mice were injected i.p. with saline or drug. Immediately following drug administration, the mice were placed individually in the cages. Beam break data was monitored and recorded for 60 min.

Elevated Plus Maze (Rats) Plus maze testing was performed and scored as previously described (Forcelli and Heinrichs, 2008; Forcelli et al., 2012), in a standard grey rat elevated plus maze (50 cm arms, elevated 40 cm off the ground [Stoelting Co., Wood Dale, Ill.]). Testing was conducted under 20 lux red light, 30 min after drug administration. The number of arm entries and time spent in open and closed arms were recorded using ANYmaze (Stoelting Co, Wood Dale, Ill.).

Marble Burying (Mice) After a 1 h period of acclimation to the testing room, the mice (n=6-10 per group) were injected i.p. with saline, EDDP, EMDP, or CDP at the doses indicated. Ten minutes later, the mice were placed individually in small cages (26×20×14 cm), in which twenty marbles had been equally distributed on top of mouse bedding (5-cm deep), and a wire lid was placed on top of the cage. Mice were left undisturbed for 15 min, after which time the number of buried marbles (i.e., those covered by bedding three-quarters or more) was counted.

Forced Swim Test (FST; Rats) The FST in rats was conducted as previously described (Porsolt et al., 2001). On day 1, rats were placed in a cylindrical chamber (20 cm in diameter, 46 cm deep) filled to a height of 38 cm with room temperature water for 15 min. After the completion of this pre-exposure test, animals were removed from the apparatus, dried with towels and placed under a heat lamp for ~30 min. Immediately prior to returning the animals to their home cage, they were treated with either EMDP (10 or 20 mg/kg), EDDP (10 mg/kg), sertraline (20 mg/kg), mecamylamine (5 mg/kg) or vehicle. Animals were treated with these same doses again 20 h and 23 h after the initial dose. Twenty-four h after the pre-exposure, animals were re-introduced to the apparatus and video-recorded for 5 min. Immobility was hand-scored for each video record by a treatment blind observer (P.A.F.) using ANYmaze (Stoelting) to record the data.

Forced Swim Test (FST; Mice) The FST in mice was conducted as previously described [20] [11]. Briefly, 10 min following i.p. injection of saline, EDDP or EMDP, mice were placed in Plexiglas cylinders filled with water (25° C.) for 6 min while being videotaped. The forced swim score for the entire 6 min test was assessed using the Cleversystems videotracking system (CleverSys) and confirmed with visual scoring by a trained observer. A mouse was judged to be immobile when making only those movements necessary to keep its head above water.

Ptosis Assessment (Rats) Eyelid ptosis in rats was assessed 15 min prior to and 15, 30, 45, and 180 min after administration of either mecamylamine (5 mg/kg) or EMDP (20 mg/kg). Ptosis was assessed as previously described (Rubin et al., 1957). Each animal was photographed while gently restrained by hand. Photographs were analyzed by a treatment blind observer (P.A.F.) and assigned a score of 0 (no ptosis, eye completely open), 1 (mild, eye partially closed), 2 (moderate, eye half closed), 3 (severe, eye ¾ closed), or 4 (complete, eye completely closed).

Statistical Analysis Data were analyzed using SPSS (IBM, Somers, N.Y.) and GraphPad Prism (GraphPad Software, La Jolla, Calif.). Normally distributed data (open field, home cage locomotor behavior, marble burying, and forced swim) were analyzed by analysis of variance. Nonparametric data (elevated plus maze, ptosis scores) were analyzed using the Kruskal-Wallis test. Post-hoc tests were performed as appropriate (Holm-Sidak corrected). The threshold for statistical significance was set as $p<0.05$.

Results

EDDP and EMDP block nicotine-stimulated $^{86}Rb^+$ efflux mediated by α3β4 and α4β2 nAChRs. The potencies of EDDP and EMDP in blocking human α3β4 and α4β2 nAChR channel function stimulated by nicotine using $^{86}Rb^+$ efflux assays were compared. It was previously shown that each of the two enantiomers of these two methadone metabolites are equipotent in blocking rat α3β4 nAChR channels (Xiao et al., 2001), and as shown in Table 1, their potencies in blocking the channel function of human α3β4 and α4β2 nAChRs were also similar. Both compounds were 2 to 2.5 times more potent at α3β4 than at α4β2 nAChRs, which was the opposite order of potency for mecamylamine, a widely used nAChR channel blocker. EDDP was 10- to 13-times more potent than EMDP at both receptor subtypes in these assays.

Because (+) and (−) enantiomers of both EDDP and EMDP demonstrated nearly equal potencies at inhibiting α3β4 and α4β2 nAChR channel function in these $^{86}Rb^+$ efflux assays, the subsequent assays were carried out with racemic mixtures of the two compounds.

TABLE 1

Inhibitory properties of enantiomers of EDDP and EMDP on function of α4β2 and α3β4 nAChR subtypes. $IC_{50}$ values were calculated from inhibition curves in which $^{86}Rb^+$ efflux was stimulated by 100 μM nicotine, as described under Materials and Methods. Mecamylamine, a noncompetitive nAChR antagonist was included for comparison. Data shown are mean ± standard error of three to six independent measurements.

| Drug | $IC_{50}$ (μM) | |
|---|---|---|
| | α4β2 nAChRs[a] | α3β4 nAChRs[a] |
| (+)-EDDP | 1.8 ± 0.6 | 0.9 ± 0.09 |
| (−)-EDDP | 1.4 ± 0.2 | 0.7 ± 0.06 |
| (+)-EMDP | 24 ± 5 | 7.4 ± 2.1 |
| (−)-EMDP | 19 ± 4 | 7.0 ± 1.2 |
| Mecamylamine | 1.0 ± 0.3 | 3.7 ± 1.2 |

[a]The defined human α4β2 and α3β4 nAChRs are stably expressed in HEK cells designated YXα4β2H1 and YXα3β4H1, respectively. See Materials and Methods for details.

Binding of methadone, EDDP and EMDP to opiate receptors labeled by [$^3$H]-naloxone. Methadone is a μ-opiate receptor agonist. EDDP, which is the N-demethylated primary metabolite of methadone, and EMDP, the secondary N-demethylated trace derivative of EDDP, are considered to be inactive at opiate receptors (Pohland et al., 1971). Consistent with this assessment, binding competition assays demonstrate that methadone competes for the majority of [$^3$H]-naloxone binding sites in rat forebrain with high affinity (~11 nM), while EDDP and EMDP compete with 84-fold and 1900-fold lower affinities, respectively.

Figure 3:
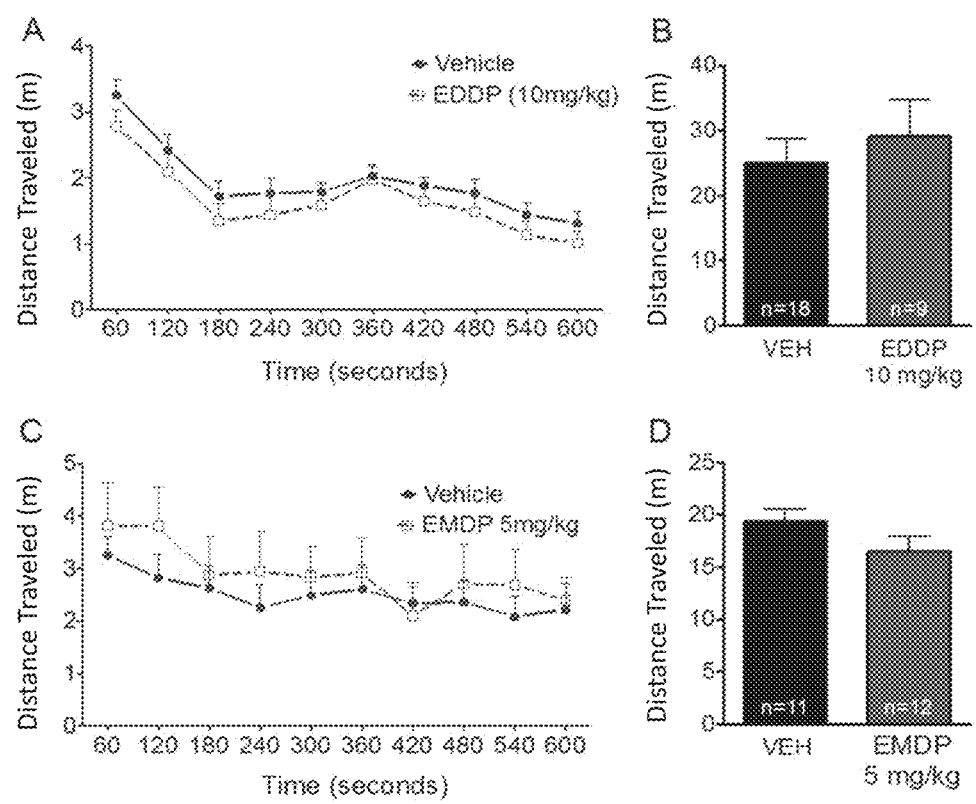
FIG. 3. EDDP and EMDP do not change rat locomotor behavior in the open field. (A) Time-course of locomotion in vehicle treated (solid line) and 10 mg/kg EDDP (broken line). (B) Total distance traveled in the 10 min test period. (C) Time-course of locomotion in vehicle treated (solid line) and 5 mg/kg EMDP (broken line). (D) Total distance traveled in the 10 min test period. n=number of animals per group.

Effects of EDDP and EMDP on Open Field Locomotor Activity in Rats. Open field locomotor activity provides an overall measure of spontaneous motor activity, as well as a measure of exploratory drive, as indicated by greater degree of exploration of the center of the maze (Crawley, 1985). As shown in FIG. 3, although analysis of variance (ANOVA) showed a significant main effect of time ($F_{9,189}=15.4$, $p<0.0001$), both control and treated rats habituated to the open field at similar rates and traveled a similar distance over the course of the test. There was no main effect of treatment ($F_{1,25}=0.54$, $p=0.54$) nor a treatment-by-time interaction ($F_{9,225}=0.56$, $p=0.83$). Thus, neither EDDP nor EMDP significantly altered open field locomotor activity in rats.

Figure 4:
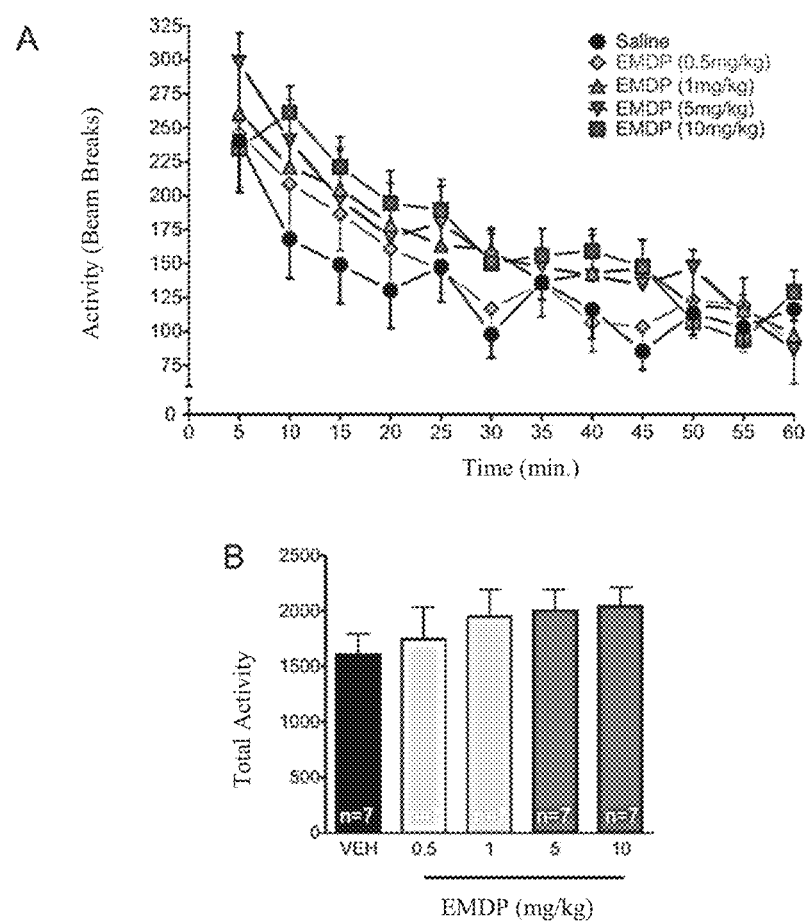
FIG. 4. EMDP does not change home cage locomotor activity in mice. (A) Time-course of locomotor activity after vehicle (circle) or EMDP: 0.5 mg/kg=diamond, 1 mg/kg=upward triangle, 5 mg/kg=downward triangle, 10 mg/kg=square. (B) Total activity. n=number of animals per group.

Effects of EMDP on Locomotor Activity in Mice. Consistent with the results in rats, ANOVA indicated that the general locomotor activity of mice placed in the novel cage decreased with time (FIG. 4A; $F_{11,330}=38.79$, $p<0.0001$). Again. EMDP did not significantly affect overall locomotor activity (FIG. 4B, $F_{4,30}=0.73$, $p=0.58$), nor was there a treatment-by-time interaction ($F_{44,330}=1.08$, $p=0.34$). EDDP was not tested in for locomotor activity in mice.

Anxiolytic-like effects in rats: Elevated Plus Maze. To examine the potential anxiolytic effects of EDDP and EMDP, the elevated plus maze was used, a standard test for anxiety-like behavior in rodents (Carobrez and Bertoglio, 2005). This test exploits the natural exploratory drive of rodents by pitting the relative safety of the dimly lighted closed arms of the maze against the open, unenclosed, elevated spaces, which are presumed to be anxiety-inducing (Pellow et al., 1985). The rats were tested in the EPM 30 min after drug treatment.

Figure 5:
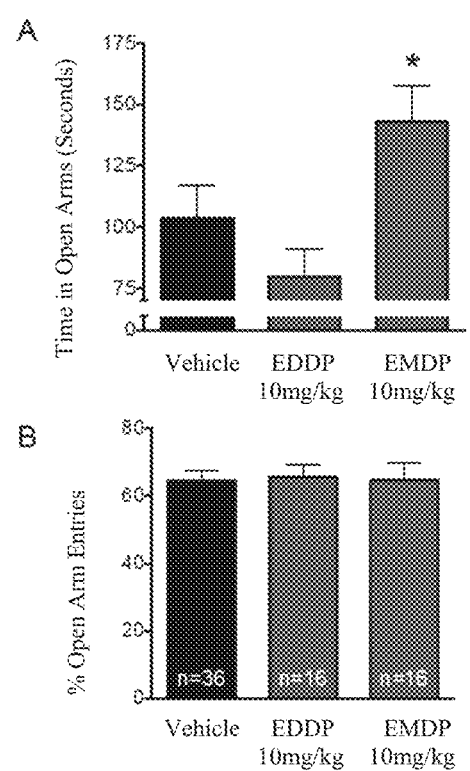
FIG. 5. Anxiolytic-like effect of EMDP, but not EDDP, measured using the elevated plus maze in rats. (A) Time that the rats spent in the open arms of the elevated plus maze. (B) Percent of total entries that were made into the open arms of the plus maze. n=number of animals per group. *=Significantly different from control (p<0.05; Kruskal-Wallis test with Dunn's post-hoc).

As shown in FIG. 5A, vehicle-treated control rats spent a mean duration of 104 s in the open arms of the elevated plus maze; whereas rats treated with EDDP (10 mg/kg) spent a mean duration of 80 s in the open arms, which was not statistically different from controls. In contrast, rats treated with EMDP spent a mean duration of 143 s in the open arms, which was statistically different from controls (Kruskal-Wallis test, $H(2)=7.1$, $p<0.05$; $p<0.05$, Dunn's multiple comparison test), suggesting that EMDP has an anxiolytic effect in this test. As shown in FIG. 5B, the groups did not differ with respect to percentage of entries made into the open arms of the plus maze. Finally, the latency to first entry in the open arms did not differ as a function of treatment group (data not shown).

Anxiolytic-like effects in mice: Marble-burying test. Marble burying is a natural tendency of mice and rats (Poling et al., 1981; Njung'e and Handley, 1991). Although this behavior itself does not necessarily reflect a state of anxiety in rodents (Njung'e and Handley, 1991; Thomas et al., 2009; Wurzman et al., 2014), inhibition of this behavior does appear to reliably distinguish antianxiety drugs (Broekkamp et al., 1986; Njung'e and Handley, 1991; Nicolas et al., 2006). Therefore, we examined the effects of EDDP and EMDP on this behavior.

Figure 6:
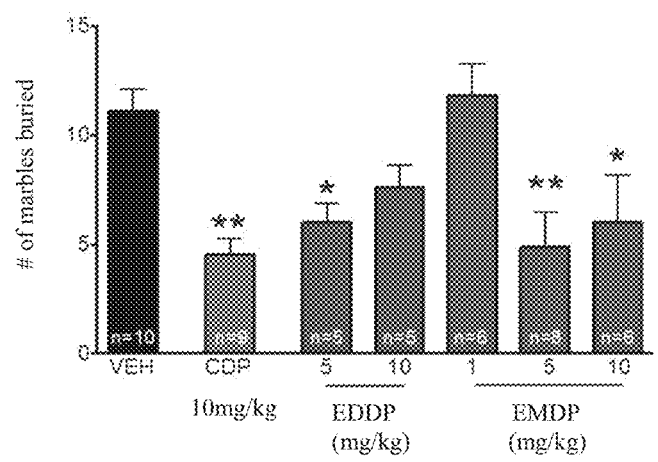
FIG. 6. Anxiolytic-like effects of EDDP and EMDP measured using the marble-burying task in mice. The number of marbles buried out of 20 in the 15-minute test after injection with chlordiazepoxide (CDP), EDDP or EMDP at the doses shown. n=number of animals per group. Significantly different from control (*p<0.05; **p<0.01; analysis of variance with Holm-Sidak post-hoc test).

Mice were injected i.p. with saline (vehicle), CDP (positive control), EDDP, or EMDP at the doses shown. Ten minutes after injection, the mice were placed individually in small cages with 20 marbles on top of the bedding, and 15 min later the number of marbles buried was counted. As shown in FIG. 6, vehicle-treated control mice buried a mean of 11 marbles during the 15 min test. As expected, animals treated with the positive control CDP (10 mg/kg) buried significantly fewer marbles than vehicle treated animals ($p<0.01$). Mice treated with EDDP at a dose of 5 mg/kg also buried significantly fewer marbles than did controls ($p<0.05$), but at the higher dose of 10 mg/kg, this did not reach statistical significance. Mice treated with EMDP buried significantly fewer marbles at both the 5 mg/kg ($p<0.01$) and 10 mg/kg dose ($p<0.05$), but not at the 1 mg/kg dose. These effects were analyzed by post-hoc tests (Holm-Sidak corrected) after analysis of variance revealed a significant main effect of drug treatment ($F_{6,42}=5.49$, $p=0.0005$).

Figure 7:
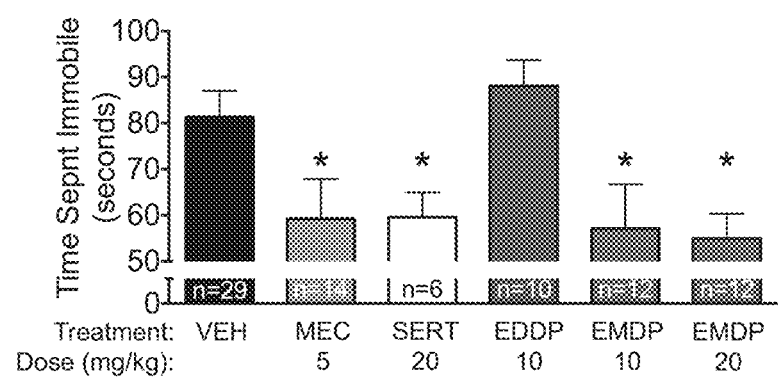
FIG. 7. Antidepressant-like effect of EMDP, but not EDDP, in the rat forced swim task. Time spent immobile during the 5-min forced swim test after injection with mecamylamine (MEC), sertraline (SERT), EDDP or EMDP at the doses shown. Significantly different from control (*p<0.05; analysis of variance with Holm-Sidak post-hoc test).

Antidepressant-like effects in rats: Forced swim test. The FST (Porsolt et al., 1977) is a well-established assay with predictive utility for antidepressant drug efficacy. As shown in FIG. 7, vehicle-treated rats spent a mean duration of 81 s immobile during the 5 min forced swim test. Treatment of rats with sertraline (20 mg/kg), an antidepressant used here as a positive control, significantly reduced immobile time ($p<0.05$). Similarly, treatment of rats with the nAChR channel blocker mecamylamine (5 mg/kg), which also reduces immobile time in this test (Caldarone et al., 2004; Andreasen and Redrobe, 2009) and which also may have antidepressant activity (Lippiello et al., 2008) reduced immobile time ($p<0.05$). Treatment with EDDP (10 mg/kg) was without effect in this test, but treatment with EMDP at both 10 and 20 mg/kg reduced immobile time ($p<0.05$) to the same extent as sertraline (Holm-Sidak corrected post-hoc tests after ANOVA showed a significant main effect of treatment ($F_{5,76}=3.489$, $p<0.001$).

Figure 8:
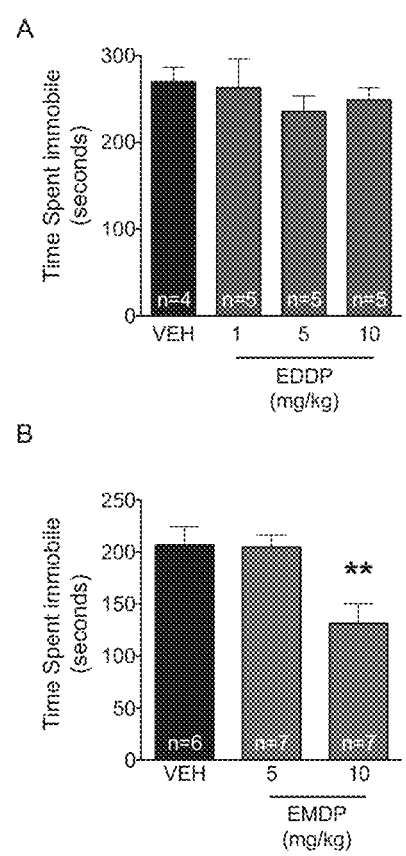
FIG. 8. Antidepressant-like effect of EMDP, but not EDDP, in the mouse forced swim task. Time spent immobile during the 5-min forced swim test. (A) EDDP at the doses shown did not decrease time spent immobile. (B) EMDP at a dose of 10 mg/kg did decrease time spent immobile. **p<0.01, analysis of variance with Holm-Sidak post-hoc test.

Antidepressant-like effects in mice: Forced Swim Test. As shown in FIG. 8A, vehicle treated controls spent a mean duration of 270 s immobile during the 6 min forced swim test. Treatment of mice with 1, 5, or 10 mg/kg EDDP did not produce a significant effect on duration of immobility ($F_{3,15}=0.45$, $p=0.72$). In contrast, in separate experiments using different groups of mice, EMDP reduced immobility time. Thus as shown in FIG. 8B, in these experiments vehicle treated mice spent a mean duration of 207 s immobile during this 6 min forced swim test. EMDP at a dose of 5 mg/kg did not affect immobility time, but at a dose of 10 mg/kg it significantly reduced it (ANOVA and one-tailed Holm-Sidak corrected post-hoc tests ($F_{2,17}=7.128$, $p<0.01$).

Figure 9:
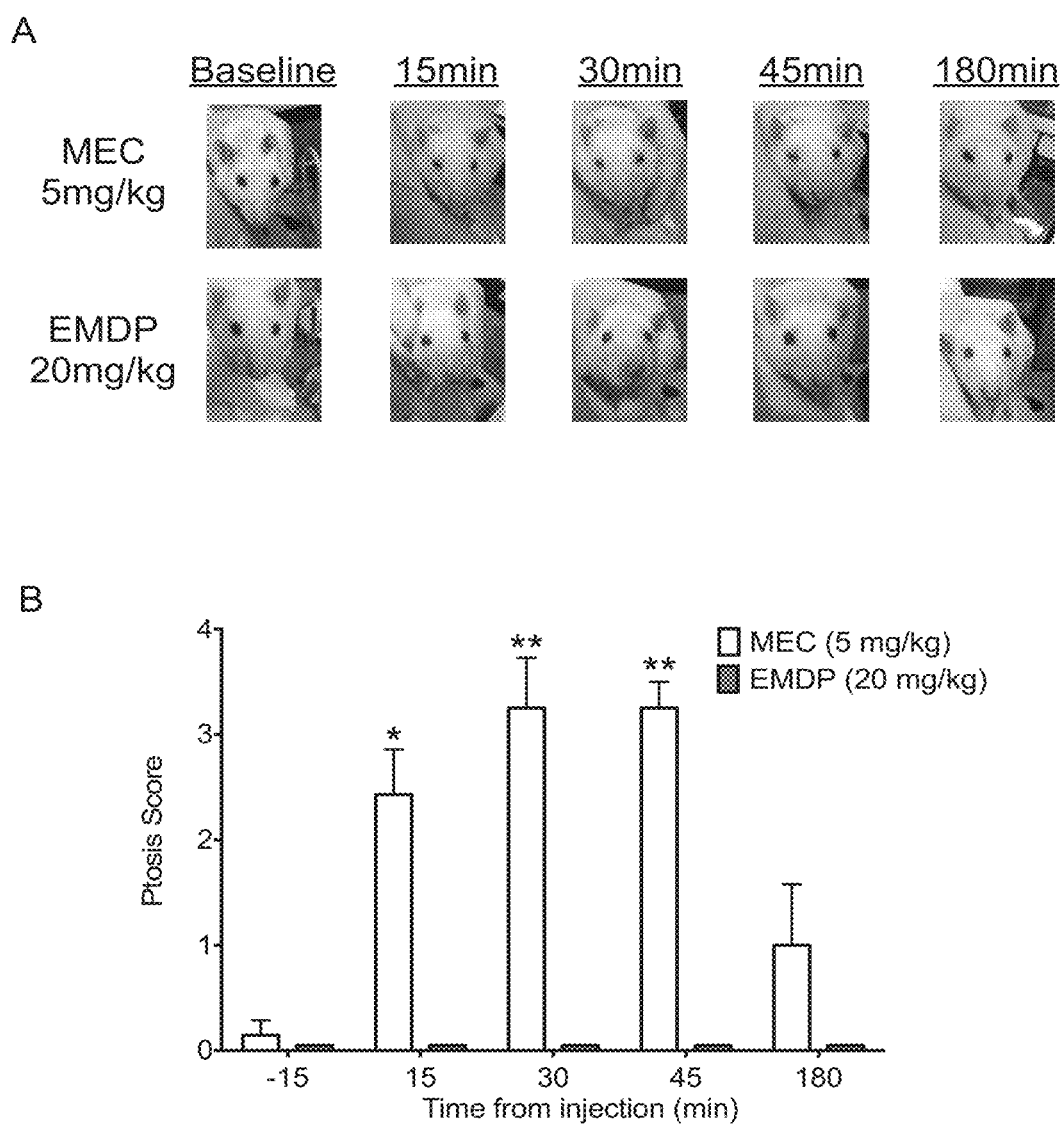
FIG. 9. Mecamylamine, but not EMDP results in ptosis in the rat. (A) Representative photographs of animals treated with mecamylamine (5 mg/kg) or EMDP (20 mg/kg), at each observation time (B) Quantification of ptosis severity at 15 min intervals. n in both groups. *p<0.05, **p<0.01; Kruskal-Wallis test with Dunn's post-hoc.

Comparison of ganglionic effects of mecamylamine and EMDP in rats. Ganglionic blockade can cause eyelid ptosis; and indeed, during forced swim tests in rats, we observed obvious ptosis in response to mecamylamine (5 mg/kg). But interestingly, EMDP at doses (10 and 20 mg/kg) equally efficacious in the FST did not produce ptosis. To examine this difference in more detail, an additional group of rats was treated with either mecamylamine (5 mg/kg) or EMDP (20 mg/kg) and ptosis was observed and quantified over the course of 3 h. Mecamylamine produced ptosis in a time-dependent manner (Kruskal-Wallis test, $H(4)=16.63$, $p<0.005$), with onset within 15 min after injection, and statistically significant effects still apparent at 30 and 45 min, but not at 3 h after injection (FIG. 9). In contrast, ptosis was not apparent at any time during the 3 h observation period in animals treated with EMDP (FIG. 9).

Discussion

Previous studies found that both EDDP and EMDP blocked rat α3β4 nAChR channels (Xiao et al., 2001), and here we show that they do the same at human α3β4 and α4β2 nAChR channels. Our evaluations of these two compounds in three behavioral tests predictive of anxiolytic and/or antidepressant activity in rodents indicate that EMDP, in particular, shows positive effects in each of these tests in both rats and mice. The pattern of behavioral responses to EMDP was consistent across tasks and species. Moreover, the efficacy of EMDP in these behavioral tests was similar to chlordiazepoxide and sertraline, standard positive control anxiolytic and antidepressant compounds, respectively. In contrast. EDDP produced a significant effect only in the marble burying test in mice and then only at one dose, while a higher dose did not produce significant effects in the same test.

The striking difference in efficacy between EDDP and EMDP in these behavioral assays is opposite to the potencies of these two compounds in blocking both α3β4 and α4β2 nAChR channel function in the $^{86}Rb^{+}$ assays in vitro.

Importantly, while EMDP produced a robust effect in these preclinical tests for anxiolytic and antidepressant activity in both rats and mice, it did not significantly affect locomotor activity in either species. Moreover. EMDP even at the highest dose used in these studies in the rat did not produce eyelid ptosis, which is a common feature of drugs such as mecamylamine that block nAChRs in autonomic ganglia. This may be because EMDP is only half as potent as mecamylamine in blocking human α3β4 nAChRs and only one-sixth as potent in blocking rat α3β4 nAChRs (Xiao et al, 2001), which are important for ganglionic function (Xu et al., 1999; Mao et al., 2006).

There is a substantial literature supporting nAChRs as potential targets for treatment of affective disorders (File et al., 1998; Mineur and Picciotto, 2010; see below). Indeed, studies in rodents demonstrate bimodal effects of nicotinic agonists on anxiety-related behaviors, with low doses of agonists eliciting anxiolytic-like behaviors and higher doses evoking anxiogenic-like behaviors (File et al., 1998; Anderson and Brunzell, 2012; Varani et al., 2012). In fact, low doses of nicotine and the nAChR competitive antagonist dihydro-β-erythroidine produced similar effects in these behavioral studies (Anderson and Brunzell, 2012), suggesting that desensitization of nAChRs by low (possibly sub-activating) doses of nicotine are anxiolytic, while higher doses, which initially activate the receptors, elicit an anxiogenic response, perhaps involving downstream GABA-B receptors (Varani et al., 2012).

The results from the studies here do not help to determine whether the effects of EMDP in these preclinical tests for anxiolytic and antidepressant activity involve primarily α3β4* or α4β2* nAChRs. or both. Although EMDP is about twice as potent blocking α3β4 as α4β2 nAChRs, previous studies have implicated β2-containing nAChRs in antidepressant (Tizabi et al., 1999; Rabenstein et al., 2006; Mineur et al., 2007) and anxiolytic actions (Turner et al., 2010, 2011, 2013; Anderson and Brunzell, 2012; 2015) of nicotinic agonists and antagonists. In fact, both of these receptors could be involved, as well as other nAChR subtypes, including α7 (Rabenstein et al., 2006). Moreover, the data does not exclude an effect of EMDP on opiate receptors, some of which appear to acutely mediate anxiolytic and/or anxiogenic effects of some opiates (Vant Veer and Carlezon, 2013; Rorick-Kehn et al., 2014). Nevertheless, hyperactivity of the cholinergic system has long been hypothesized to be a marker for affective disorders (Janowsky et al., 1972, 1974, 1994; Mineur and Picciotto, 2010). Furthermore, it has been suggested that nicotine use (i.e., smoking) may be, in part, an attempt at self-medication of these disorders (Mineur and Picciotto, 2010). Consistent with this suggestion, it is estimated that nearly one-half of all cigarettes smoked in the US are consumed by persons suffering from some degree of a neuropsychiatric disorder (Dani and Harris, 2005).

The seeming discrepancy between the data here, which indicate that a methadone metabolite that blocks nAChRs may have potential as an antianxiety and/or antidepressant drug, and the use of the quintessential nAChR agonist nicotine (e.g., smoking) to relieve anxiety and/or depression is more apparent than real, because in virtually all cases where it has been studied, administration of nicotine rapidly and potently desensitizes nAChRs, both in vivo (Balfour, 1980; Sharp and Beyer, 1986; Hulihan-Giblin et al., 1990; for review, see Buccafusco et al., 2009) and in vitro (Grady et al., 1994; Marks et al., 1994; Lester and Dani, 1995; Pidoplichko et al., 1997; Lu et al., 1999; Paradiso and Steinbach, 2003). In fact, nicotine is much more potent in desensitizing these receptors than in activating them (Hulihan-Giblin et al., 1990; Lu et al., 1999). Moreover, the desensitizing effects of nicotine last so much longer than its brief agonist effects that nicotine can reasonably be considered a time-averaged antagonist (Hulihan-Giblin et al., 1990).

REFERENCES

Anderson S M and Brunzell D H (2012) Low dose nicotine and antagonism of 02 subunit containing nicotinic acetylcholine receptors have similar effects on affective behavior in mice. PloS One 7e48665.

Anderson S M and Brunzell D H (2015) Anxiolytic-like and anxiogenic-like effects of nicotine are regulated via diverse action at β2* nAChRs. Brit J Pharmacol 172: 2864-2877 (epub Mar. 24, 2015).

Bacher I, Wu B, Shytle D R, and George T P (2009) Mecamylamine—a nicotinic acetylcholine receptor antagonist with potential for the treatment of neuropsychiatric disorders. Expert Opin Pharmacother 10:2709-2721.

Balfour D J (1980) Studies on the biochemical and behavioral effects of oral nicotine. Arch Int Pharmacodyn Ther 245:95-103.

Belluardo N, Mudo' G, Bonomo A, Di Liberto V, Frinchi M, and Fuxe K (2008) Nicotine-induced fibroblast growth factor-2 restores the age-related decline of precursor cell proliferation in the subventricular zone of rat brain. Brain Res 1193:12-24.

Bertrand D (2005) The possible contribution of neuronal nicotinic acetylcholine receptors in depression. Dialogues Clin Neurosci 7:207-216.

Broekkamp C L, Rijk H W, Joly-Gelouin D, and Lloyd K L (1986) Major tranquillizers can be distinguished from minor tranquillizers on the basis of effects on marble burying and swim-induced grooming in mice. Eur J Pharmacol 126:223-229.

Buccafusco J J, Beach J W, Terry A V (2009) Desensitization of nicotinic acetylcholine receptors as a strategy for drug development. J Pharmacol. Exp Ther 328:364-370.

Caldarone B J, Wang D, Paterson N E, Manzano M, Fedolak A, Cavino K, Kwan M, Hanania T, Chellappan S K, Kozikowski A P, Olivier B, Picciotto M R, and Ghavami A (2011) Dissociation between duration of action in the forced swim test in mice and nicotinic acetylcholine receptor occupancy with sazetidine, varenicline, and 5-I-A85380. Psychopharmacology (Berl) 217:199-210.

Carobrez A P, and Bertoglio L J (2005) Ethological and temporal analyses of anxiety-like behavior: the elevated plus-maze model 20 years on. Neurosci Biobehav Rev 29:1193-1205.

Crawley J N (1985) Exploratory behavior models of anxiety in mice. Neurosci Biobehav Rev 9:37-44.

Dani J A, and Harris R A (2005) Nicotine addiction and comorbidity with alcohol abuse and mental illness. Nat Neurosci 8:1465-1470.

Eisch A J, and Petrik D (2012) Depression and Hippocampal Neurogenesis: A Road to Remission? Science 338:72-75.

Ferguson S M, Brodkin J D, Lloyd G K, and Menzaghi F (2000) Antidepressant-like effects of the subtype-selective nicotinic acetylcholine receptor agonist, SIB-1508Y, in the learned helplessness rat model of depression. Psychopharmacology (Berl) 152:295-303.

File S E, Kenny P J, and Ouagazzal A M (1998) Bimodal modulation by nicotine of anxiety in the social interaction test: role of the dorsal hippocampus. Behav Neurosci 112:1423-1429.

Forcelli P A, and Heinrichs S C (2008) Teratogenic effects of maternal antidepressant exposure on neural substrates of drug-seeking behavior in offspring. Addict Biol 13:52-62.

Forcelli P A, Kozlowski R, Snyder C, Kondratyev A, and Gale K (2012) Effects of neonatal antiepileptic drug exposure on cognitive, emotional, and motor function in adult rats. J Pharmacol Exp Ther 340:558-566.

Glassman A H, Helzer J E, Covey L S, Cottler L B, Stetner F, Tipp J E, and Johnson J (1990) Smoking, smoking cessation, and major depression. JAMA 264:1546-1549.

Grady S R, Marks M J, and Collins A C (1994) Desensitization of nicotine-stimulated [3H]dopamine release from mouse striatal synaptosomes. *J Neurochem* 62:1390-1398.

Hulihan-Giblin B A, Lumpkin M D, and Kellar K J (1990) Acute effects of nicotine on prolactin release in the rat: agonist and antagonist effects of a single injection of nicotine. *J Pharmacol Exp Ther* 252:15-20.

Hussmann G P, DeDominicis K E, Turner J R, Yasuda R P, Klehm J, Forcelli P A, Xiao Y, Richardson J R, Sahibzada N, Wolfe B B, Lindstrom J, Blendy J A, and Kellar K J (2014) Chronic sazetidine-A maintains anxiolytic effects and slower weight gain following chronic nicotine without maintaining increased density of nicotinic receptors in rodent brain. *J Neurochem* 129:721-731.

Isiegas C, Mague S D, and Blendy J A (2009) Sex differences in response to nicotine in C57Bl/6:129SvEv mice. *Nicotine Tob Res Off J Soc Res Nicotine Tob* 11:851-858.

Janowsky D S, el-Yousef M K, and Davis J M (1974) Acetylcholine and depression. *Psychosom Med* 36:248-257.

Janowsky D S, el-Yousef M K, Davis J M, and Sekerke H J (1972) A cholinergic-adrenergic hypothesis of mania and depression. *Lancet* 2:632-635.

Janowsky D S, Overstreet D H, and Nurnberger J I (1994) Is cholinergic sensitivity a genetic marker for the affective disorders? *Am J Med Genet* 54:335-344.

Kessler R C, Chiu W T, Demler O, Merikangas K R, and Walters E E (2005) Prevalence, severity, and comorbidity of 12-month DSM-IV disorders in the National Comorbidity Survey Replication. *Arch Gen Psychiatry* 62:617-627.

Ledford H (2011) Depression drug disappoints. *Nature* 479:278.

Lester R A, and Dani J A (1995) Acetylcholine receptor desensitization induced by nicotine in rat medial habenula neurons. *J Neurophysiol* 74:195-206.

Lippiello P M, Beaver J S, Gatto G J, James J W, Jordan K G, Traina V M, Xie J, and Bencherif M (2008) TC-5214 (S-(+)-mecamylamine): a neuronal nicotinic receptor modulator with antidepressant activity. *CNS Neurosci Ther* 14:266-277.

Lu Y, Marks M J and Collins A C (1999) Desensitization of nicotinic agonist-induced [3H]-ϒ-aminobutyric acid release from mouse brain synaptosomes is produced by subactivating concentrations of agonists.

Mackler S, Pacchioni A, Degnan R, Homan Y, Conti A C, Kalivas P, and Blendy J A (2008) Requirement for the POZ/BTB protein NAC1 in acute but not chronic psychomotor stimulant response. *Behav Brain Res* 187:48-55.

Mao D, Yasuda R P, Fan H, Wolfe B B, and Kellar K J (2006) Heterogeneity of nicotinic cholinergic receptors in rat superior cervical and nodose ganglia. *Mol Pharmacol* 70:1693-1699.

Marks M J, Grady S R, Yang J M, Lippiello P M, and Collins A C (1994) Desensitization of nicotine-stimulated 86Rb+ efflux from mouse brain synaptosomes. *J Neurochem* 63:2125-2135.

McGranahan T M, Patzlaff N E, Grady S R, Heinemann S F, and Booker T K (2011) α4β2 nicotinic acetylcholine receptors on dopaminergic neurons mediate nicotine reward and anxiety relief. *J Neurosci Off J Soc Neurosci* 31:10891-10902.

McKay B E, Placzek A N, and Dani J A (2007) Regulation of synaptic transmission and plasticity by neuronal nicotinic acetylcholine receptors. *Biochem Pharmacol* 74:1120-1133.

Mineur Y S, and Picciotto M R (2010) Nicotine receptors and depression: revisiting and revising the cholinergic hypothesis. *Trends Pharmacol Sci* 31:580-586.

Mineur Y S, Somenzi O, and Picciotto M R (2007) Cytisine, a partial agonist of high-affinity nicotinic acetylcholine receptors, has antidepressant-like properties in male C57BL/6J mice. *Neuropharmacology* 52:1256-1262.

Mudò G, Belluardo N, Mauro A, and Fuxe K (2007) Acute intermittent nicotine treatment induces fibroblast growth factor-2 in the subventricular zone of the adult rat brain and enhances neuronal precursor cell proliferation. *Neuroscience* 145:470-483.

National Research Council (U.S.), Institute for Laboratory Animal Research (U.S.), and National Academies Press (U.S.) (2011) *Guide for the care and use of laboratory animals*, 8th ed, National Academies Press, Washington, D.C.

Nickell J R, Grinevich V P, Siripurapu K B, Smith A M, and Dwoskin L P (2013) Potential therapeutic uses of mecamylamine and its stereoisomers. *Pharmacol Biochem Behav* 108:28-43.

Nicolas L B, Kolb Y, and Prinssen E P M (2006) A combined marble burying-locomotor activity test in mice: a practical screening test with sensitivity to different classes of anxiolytics and antidepressants. *Eur J Pharmacol* 547:106-115.

Njung'e K, and Handley S L (1991) Effects of 5-HT uptake inhibitors, agonists and antagonists on the burying of harmless objects by mice; a putative test for anxiolytic agents. *Br J Pharmacol* 104:105-112.

Paperwalla K N, Levin T T, Weiner J, and Saravay S M (2004) Smoking and depression. *Med Clin North Am* 88:1483-1494, x-xi.

Paradiso K G, and Steinbach J H (2003) Nicotine is highly effective at producing desensitization of rat alpha4beta2 neuronal nicotinic receptors. *J Physiol* 553:857-871.

Pellow S, Chopin P, File S E, and Briley M (1985) Validation of open:closed arm entries in an elevated plus-maze as a measure of anxiety in the rat. *J Neurosci Methods* 14:149-167.

Pidoplichko V I, DeBiasi M, Williams J T, and Dani J A (1997) Nicotine activates and desensitizes midbrain dopamine neurons. *Nature* 390:401-404.

Pohland A, Boaz H E, and Sullivan H R (1971) Synthesis and identification of metabolites resulting from the biotransformation of DL-methadone in man and in the rat. *J Med Chem* 14:194-197.

Poling A, Cleary J, and Monaghan M (1981) Burying by rats in response to aversive and nonaversive stimuli. *J Exp Anal Behav* 35:31-44.

Porsolt R D, Bertin A, and Jalfre M (1977) Behavioral despair in mice: a primary screening test for antidepressants. *Arch Int Pharmacodyn Ther* 229:327-36.

Porsolt R D, Brossard G, Hautbois C, and Roux S (2001) Rodent models of depression: forced swimming and tail suspension behavioral despair tests in rats and mice. *Curr Protoc Neurosci Editor Board Jacqueline N Crawley Al* Chapter 8:Unit 8.10A.

Rabenstein R L, Caldarone B J, and Picciotto M R (2006) The nicotinic antagonist mecamylamine has antidepressant-like effects in wild-type but not beta2- or alpha7-nicotinic acetylcholine receptor subunit knockout mice. *Psychopharmacology (Berl)* 189:395-401.

Rorick-Kehn L M, Witkin J M, Statnick M A, Eberle E, McKinzie J H, Kahl S D, Forster B M, Wong C J Xia L, Crile R S et al. (2014) LY2456302 is a novel, potent, orally-bioavailable small molecule kapp-selective antagonist with activity in animal models predictive of efficacy in mood and addictive disorders. *Neuropharmacology* 77:131-144.

Rubin B, Malone M H, Waugh M H, and Burke J C (1957) Bioassay of Rauwolfia roots and alkaloids. *J Pharmacol Exp Ther* 120:125-136.

Sharp B M, and Beyer H S (1986) Rapid desensitization of the acute stimulatory effects of nicotine on rat plasma adrenocorticotropin and prolactin. *J Pharmacol Exp Ther* 238:486-491.

Shytle R D, Silver A A, Sheehan K H, Sheehan D V, and Sanberg P R (2002) Neuronal nicotinic receptor inhibition for treating mood disorders: preliminary controlled evidence with mecamylamine. *Depress Anxiety* 16:89-92.

Thomas A, Burant A, Bui N, Graham D, Yuva-Paylor L A, and Paylor R (2009) Marble burying reflects a repetitive and perseverative behavior more than novelty-induced anxiety. *Psychopharmacology (Berl)* 204:361-373.

Tizabi Y, Overstreet D H, Rezvani A H, Louis V A, Clark E, Janowsky D S, and Kling M A (1999) Antidepressant effects of nicotine in an animal model of depression. *Psychopharmacology (Berl)* 142:193-199.

Trivedi M H, Rush A J, Wisniewski S R Nierenberg A A, Warden D, Ritz L, Norquist G, Howland R H, Lebowitz B, McGrath P J, Shores-Wilson K, Biggs M M, Balasubramani G K, Fava M, and STAR*D Study Team (2006) Evaluation of outcomes with citalopram for depression using measurement-based care in STAR*D: implications for clinical practice. *Am J Psychiatry* 163:28-40.

Turner J R, Castellano L M, and Blendy J A (2010) Nicotinic partial agonists varenicline and sazetidine-A have differential effects on affective behavior. *J Pharmacol Exp Ther* 334:665-672.

Turner J R, Castellano L M, and Blendy J A (2011) Parallel anxiolytic-like effects and upregulation of neuronal nicotinic acetylcholine receptors following chronic nicotine and varenicline. *Nicotine Tob Res Off J Soc Res Nicotine Tob* 13:41-46.

Turner J R, Wilkinson D S, Poole R L, Gould T J, Carlson G C, and Blendy J A (2013) Divergent functional effects of sazetidine-a and varenicline during nicotine withdrawal. *Neuropsychopharmacol Off Publ Am Coll Neuropsychopharmacol* 38:2035-2047.

Vant Veer A and Carlezon Wm A, (2013) Role of kappa-opioid receptors in stress and anxiety-related behavior. *Psychopharmacology* 229:435-452.

Varani A P, Moutinho L M, Balerio G N (20120. Acute behavioural responses to nicotine and nicotine withdrawal syndrome are modified in GABA(B1) knockout mice. *Neuropharmacology* 63:863-872.

Vázquez-Palacios G, Bonilla-Jaime H, and Velázquez-Moctezuma J (2005) Antidepressant effects of nicotine and fluoxetine in an animal model of depression induced by neonatal treatment with clomipramine. *Prog Neuropsychopharmacol Biol Psychiatry* 29:39-46.

Walters C L, and Blendy J A (2001) Different requirements for cAMP response element binding protein in positive and negative reinforcing properties of drugs of abuse. *J Neurosci Off J Soc Neurosci* 21:9438-9444.

Wurzman R, Forcelli P A, Griffey C J, and Kromer L F (2014) Repetitive grooming and sensorimotor abnormalities in an ephrin-A knockout model for Autism Spectrum Disorders. *Behav Brain Res*, doi: 10.1016/j.bbr.2014.09.012.

Xiao Y, Meyer E L, Thompson J M, Surin A, Wroblewski J, and Kellar K J (1998) Rat alpha3/beta4 subtype of neuronal nicotinic acetylcholine receptor stably expressed in a transfected cell line: pharmacology of ligand binding and function. *Mol Pharmacol* 54:322-333.

Xiao Y, Smith R D, Caruso F S, and Kellar K J (2001) Blockade of rat alpha3beta4 nicotinic receptor function by methadone, its metabolites, and structural analogs. *J Pharmacol Exp Ther* 299:366-371.

Xiao Y, Tuan E, Sahibzada N, Tran T, A-Muhtasib N, Yasuda R, Liu Y, Yenugonda V, Paige M, Brown M, and Kellar K (2012) Comparison of pharmacological properties of human versus rat alpha4beta2 and alpha3betat4 nicotinic acetylcholine receptors stably expressed in HEK293 cells, New Orleans.

Xu W, Orr-Urtreger A, Nigro F, Gelber S, Sutcliffe C B, Armstrong D, Patrick J W, Role L W, Beaudet A L, and Biasi M D (1999) Multiorgan Autonomic Dysfunction in Mice Lacking the β2 and the β4 Subunits of Neuronal Nicotinic Acetylcholine Receptors. *J Neurosci* 19:9298-9305.

Zvolensky M J, Gonzalez A, Bonn-Miller M O, Bernstein A, and Goodwin R D (2008) Negative reinforcement/negative affect reduction cigarette smoking outcome expectancies: incremental validity for anxiety focused on bodily sensations and panic attack symptoms among daily smokers. *Exp Clin Psychopharmacol* 16:66-76.

INCORPORATION BY REFERENCE

All patents and published patent applications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

We claim:
1. A method of treating depression, comprising administering to a subject in need thereof a therapeutically effective amount of 2-ethyl-5-methyl-3,3-diphenyl-1-pyrroline (EMDP) or a pharmaceutically acceptable salt thereof.
2. The method of claim 1, wherein the subject is a human.
3. The method of claim 2, wherein the compound is administered orally.
4. The method of claim 1, wherein the compound is administered orally.

* * * * *